(12) United States Patent
Diehl

(10) Patent No.: US 7,501,604 B2
(45) Date of Patent: Mar. 10, 2009

(54) SENSOR ELEMENT FOR DETERMINING GAS COMPONENTS IN GAS MIXTURES, AND METHOD FOR MANUFACTURING IT

(75) Inventor: Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 309 days.

(21) Appl. No.: 11/294,808

(22) Filed: Dec. 5, 2005

(65) Prior Publication Data
US 2006/0151466 A1 Jul. 13, 2006

(30) Foreign Application Priority Data
Dec. 15, 2004 (DE) ............... 10 2004 060 291

(51) Int. Cl.
*H05B 1/02* (2006.01)
*G01N 27/26* (2006.01)

(52) U.S. Cl. ............ 219/494; 204/425; 204/426; 204/427; 204/428; 204/429; 204/403.01; 204/403.06; 219/448.11

(58) Field of Classification Search ............ 204/424, 204/208, 425, 426, 427, 428, 429, 403.01, 204/403.06; 219/494, 448.11
See application file for complete search history.

(56) References Cited

U.S. PATENT DOCUMENTS

| 4,668,374 A | * | 5/1987 | Bhagat et al. | ............. 204/412 |
| 5,164,068 A | * | 11/1992 | Udo et al. | ............. 204/424 |

FOREIGN PATENT DOCUMENTS

| DE | 43 43 089 | 6/1996 |
| DE | 10 2004 013 852 | 12/2005 |

* cited by examiner

*Primary Examiner*—Shawntina Fuqua
(74) *Attorney, Agent, or Firm*—Kenyon & Kenyon LLP

(57) ABSTRACT

A sensor element for determining the concentration of gas components in gas mixtures, e.g., for determining the oxygen concentration in exhaust gases of combustion engines, includes: at least one electrochemical measurement cell that encompasses a first and a second electrode in contact with a solid electrolyte material; a heating element for heating the sensor element to operating temperature; and a cavity integrated into the sensor element. The cavity exhibits, in at least one region close to the lateral delimiting surfaces of the cavity, a diameter that is greater than zero and smaller than the diameter in its central region.

19 Claims, 4 Drawing Sheets

SENSOR ELEMENT FOR DETERMINING GAS COMPONENTS IN GAS MIXTURES, AND METHOD FOR MANUFACTURING IT

FIELD OF THE INVENTION

The invention relates to a sensor element for determining gas components in gas mixtures, in particular for determining the oxygen concentration in exhaust gases of combustion engines, and a method for manufacturing the sensor element.

BACKGROUND INFORMATION

Conventional sensor elements for determining the oxygen concentration in exhaust gases of combustion engines include a planar solid electrolyte body and an electrochemical pump cell, as well as an electrochemical Nernst cell or concentration cell co-acting with the pump cell. Such oxygen sensors are also known as broadband lambda sensors.

With the aid of the electrodes of the pump cell, oxygen is pumped out of a measured gas space into the exhaust gas flow or from the exhaust gas flow into the measured gas space. For that purpose, one of the pump electrodes is mounted in the measured gas space and the other on an outer surface of the sensor element, exposed to the exhaust gas flow. The electrodes of the concentration cell are disposed so that one is likewise located in the measured gas space, but the other is located in a reference gas conduit usually filled with air. This configuration makes possible a direct comparison between the oxygen potential of the measurement electrode in the measured gas space and the reference oxygen potential of the reference electrode, in the form of a measurable voltage present at the concentration cell. In terms of measurement technology, the pump voltage to be applied to the electrodes of the pump cell is selected so that a predetermined voltage value is maintained at the concentration cell. The pump current flowing between the electrodes of the pump cell is employed as a measurement signal, proportional to the oxygen partial pressure, of the sensor element.

Because ceramic solid-electrolyte materials exhibit sufficient ion conductivity only at higher temperatures, the sensor element further includes a heating element in the form of a resistive conductor path embodied between ceramic insulating layers. This heating element serves to heat the sensor element to an operating temperature of, for example, 750 to 800° C. The voltage applied to the electrical resistance heater for this purpose is limited by the motor vehicle's own voltage.

In the context of a cold start, for example, the heating element thus requires a certain amount of time before the sensor element heats up to operating temperature and the sensor can supply a reliable measured value for the oxygen concentration in the exhaust gas. The sensor element's heating-up time is increased by heat losses to its outer surface that occur because of cooling of the sensor element by cold exhaust gas flowing past, and as a result of thermal radiation.

German patent document DE 10 2004 013 852 discloses a sensor element for determining the physical property of a measured gas, the sensor element having two cavities that are located between a heating element integrated into the sensor element and an outer surface of the heating element. As a result of the air space existing in the cavities, the sensor element's thermal radiation is decreased and the sensor element's heating-up time is shortened.

Published German patent document DE 43 43 089 describes a sensor element for determining the oxygen content in gas mixtures, in which sensor element a portion of an insulator surrounding the resistance heating element is made up of cavities integrated into the sensor element. Any influence on the measurement signals of the sensor element resulting from the heater currents flowing in the resistance heating element is thereby avoided.

A problem relating to the incorporation of cavities into ceramic sensor elements is that in the context of heating and cooling processes, thermal stresses can occur in the ceramic material and cracks can thus form in the ceramic films. If these cracks occur, for example, in the ceramic films that surround the heating element and serve as insulation, the result is a pronounced in-coupling of heater currents into the measurement signals of the sensor element, rendering the latter unusable.

It is an object of the present invention to provide a sensor element that has a short heating-up-time characteristic and good operating durability.

SUMMARY OF THE INVENTION

It has been observed that in sensor elements into which a cavity is integrated, cracking has occurred mostly at the outer edges of the sensor element in the region of the cavities. In accordance with the present invention, it is therefore particularly advantageous if, upon implementation of the sensor element, suitable measures are taken that result in a stress reduction in this region of the sensor element.

For example, the sensor element has a cavity that exhibits, in at least one region close to the lateral delimiting surfaces of the cavity, a diameter that differs from zero and is smaller than in its central region. The result of this is that at least one of the ceramic layers that delimit the cavity has a greater layer thickness in the crack-prone outer region of the sensor element than in its region remote from the outer surface, so that thermal stresses occurring in the region of the ceramic layer close to the outer surface result in smaller tensile loads than in its region remote from the outer surface, and thus in a lesser tendency to form cracks.

It is thus advantageous if at least one of the longitudinal edges of the cavity integrated into the sensor element is rounded or exhibits a chamfer, since a physical implementation of this kind is relatively easy to effect. It is additionally advantageous if the cavity inside the sensor element is located between the electrochemical measurement cell or cells and the heating element, since this arrangement achieves not only good thermal insulation of the sensor element, but additionally a low influence on the measurement signals of the sensor element as a result of currents occurring in the heating element.

In a further example embodiment, a ceramic layer of the sensor element delimiting the cavity exhibits an opening. Thermal stresses occurring in the ceramic layer are thereby further decreased. The opening may be slit-shaped.

It is furthermore advantageous if a first ceramic layer, delimiting the cavity on its side facing away from the heating element, is produced from a material that exhibits a greater thermal expansion than the material of which a second ceramic layer, delimiting the cavity on its side facing toward the heating element, is made. Because, upon heating, a lower temperature exists in the first ceramic layer remote from the heater than in the second ceramic layer close to the heater, the greater thermal expansion of the first ceramic layer remote from the heater compensates, despite the lower temperature, for the expansion occurring in the second layer close to the heater.

A further example embodiment provides for the first ceramic layer, delimiting the cavity on its side facing away from the heating element, to be produced from a material that has a higher modulus of elasticity than the material from which the second ceramic layer, delimiting the cavity on its side facing toward the heating element, is made. The first ceramic layer can in this fashion, because of its greater modulus of elasticity, absorb thermal stresses that occur. The same result may be achieved if the first ceramic layer is produced from a material that has a higher tensile strength than the material from which the second ceramic layer is made.

In another example embodiment of the present invention, a third ceramic layer, located between the first and second layers delimiting the cavity, is produced from a material that has a higher tensile strength than the material from which the first or the second ceramic layer delimiting the cavity is made.

DETAILED DESCRIPTION

Figure 1:
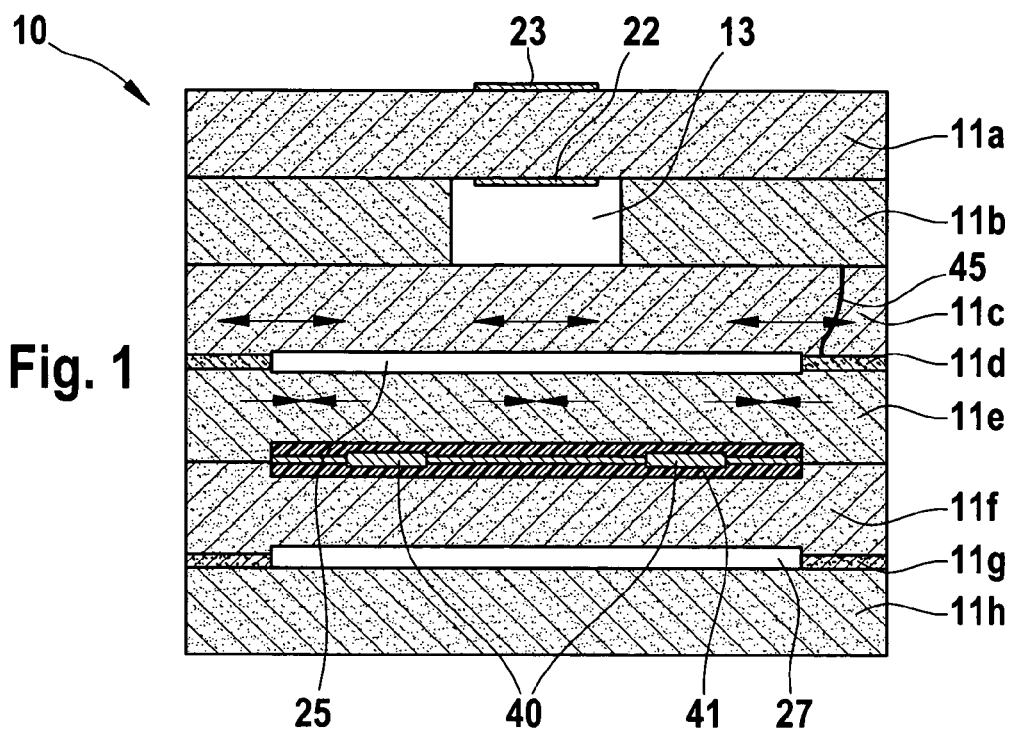
FIG. 1 shows a cross-sectional view of a conventional sensor element.

FIG. 1 shows a schematic configuration of a conventional sensor element, e.g., as described in published German patent document DE 43 43 089. A planar sensor element 10 of an electrochemical gas sensor has a plurality of oxygen ion-conducting solid electrolyte layers 11a, 11b, 11c, 11d, 11e, 11f, 11g, and 11h. Solid electrolyte layers 11a, 11b, 11c, 11e, 11f, and 11h are embodied as ceramic films, and form a planar ceramic body. They are made of an oxygen ion-conducting solid electrolyte material, for example, $ZrO_2$ stabilized or partially stabilized with $Y_2O_3$.

Solid electrolyte layers 11d and 11g, on the other hand, are produced by screen-printing a pasty ceramic material, for example, onto solid electrolyte layers 11a, 11c, and 11f. The same solid electrolyte material of which solid electrolyte layers 11a, 11b, 11c, 11e, 11f, and 11h are made is preferably also used as the ceramic component of the pasty material.

The integrated shape of the planar ceramic body of sensor element 10 is manufactured by laminating together ceramic films 11a, 11b, 11c, 11e, 11f imprinted with solid electrolyte layers 11d, 11g and with functional layers, and then sintering the laminated structure.

On the large surface of sensor element 10 directly facing the gas mixture, there is disposed on solid electrolyte layer 11a an outer measurement electrode 23 that can be covered with a porous protective layer (not depicted). A reference electrode 22 associated therewith is configured in a reference gas conduit 13, which is embodied, e.g., as a cavity, in contact with a reference gas atmosphere. Alternatively, reference gas conduit 13 can also be filled with a porous ceramic material.

Measurement electrode 23 and reference electrode 22 together form a Nernst cell or concentration cell. The potential difference occurring at electrodes 22, 23 is employed as a measurement signal proportional to the oxygen concentration of the measured gas.

To ensure that a thermodynamic equilibrium of the gas mixture components is established at electrodes 22, 23 of the sensor element, electrodes 22, 23 are made of a catalytically active material, for example platinum. In a conventional manner, the electrode material is used for all the electrodes as a cermet in order to sinter with the ceramic films.

A resistance heater 40 is furthermore integrated into solid electrolyte layers 11e and 11f, and is embedded into an electrical insulator 41, made of $Al_2O_3$, for example. By means of resistance heater 40, sensor element 10 is heated to an appropriate operating temperature of, for example, 750° C.

In order to decrease sensor element heat losses with respect to the surrounding gas mixture on the one hand, and also to prevent currents occurring in resistance heater 40 from being coupled into the measurement signals of the sensor element, cavities 25, 27, which are configured in extended planar fashion and preferably completely cover the heating region of resistance heater 40, are provided respectively between solid electrolyte layers 11c and 11e, and 11f and 11h.

As sensor element 10 heats up, thermal stresses occur in the layered composite of the sensor element. For example, compressive stresses occur in solid electrolyte layer 11e, whereas conversely, tensile stresses are produced in solid electrolyte layer 11c. This is indicated correspondingly in FIG. 1 by arrows. In unfavorable cases, cracks can occur in the individual solid electrolyte layers as a result of the thermal stresses. One such crack 45 occurs, in particular, in the regions of the solid electrolyte layers close to the outer surface.

To solve this problem, the present invention provides at least one of the cavities of the sensor element in such a way that the cavity exhibits, in at least one region close to the lateral delimiting surfaces of the cavity, a diameter that is greater than zero and smaller than the diameter in its central region. An example embodiment of the present invention is depicted in FIG. 2, in which identical reference characters designate components identical to those in FIG. 1.

Figure 2:
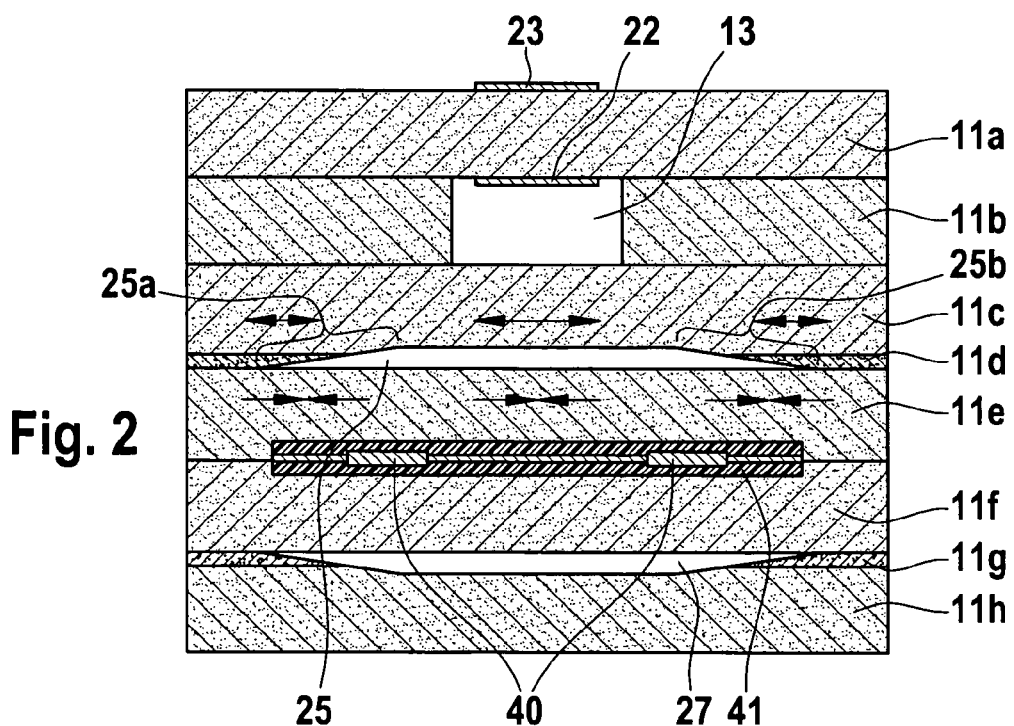
FIG. 2 shows a cross-sectional view of a first example embodiment of a sensor element according to the present invention.

It is apparent from FIG. 2 that cavity 25 has, in its regions 25a, 25b close to the outer surfaces, a height that diminishes continuously toward the lateral limits of the cavity. Cavity 25 thus has a greater diameter in its region close to the center axis of the sensor element than in its regions 25a, 25b close to the lateral limits of cavity 25. It may be alternatively or additionally provided, as depicted in FIG. 2, to embody not only cavity 25 but also cavity 27 in beveled form. Corresponding arrows in solid electrolyte layer 11c indicate that thermal stresses that occur in the edge regions of solid electrolyte layer 11c upon heating of the sensor element turn out to be much smaller than in the case of the sensor element in FIG. 1, because of greater layer thickness of the edge regions of solid electrolyte layer 11c. The formation of cracks in regions of solid electrolyte layer 11c or 11h close to the outer surface is thereby effectively prevented.

Figure 2A:
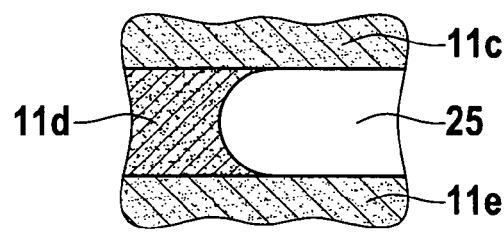
FIGS. 2a to 2d each show a variation of the cavity included in the embodiment of the sensor element shown in FIG. 2.
Figure 2B:
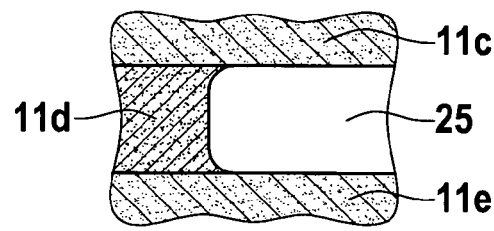
Figure 2C:
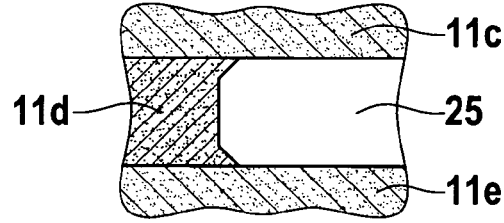
Figure 2D:
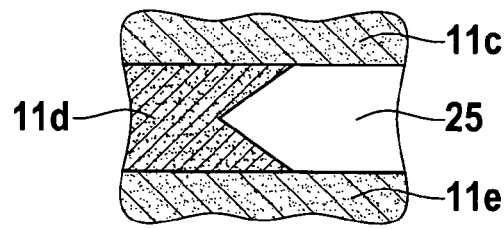

Cavities 25, 27 may also be embodied in a rounded shape as depicted in FIGS. 2a and 2b, rather than in a beveled shape, in their regions close to the lateral delimiting surfaces. Alternatively, it is also possible to provide the edges of cavities 25, 27 with a chamfer, as depicted in FIGS. 2c and 2d.

Corresponding cavities 25, 27 that have, in the regions 25a, 25b close to the outer surfaces of the sensor element, a height continuously diminishing toward the lateral limits of the cavity can be generated by the fact that during the sensor element manufacturing process, solid electrolyte layers 11d, 11g enclosing cavities 25, 27 are produced by way of multiple, successively-occurring printing steps, with multiple layers that differ in their area coverage and made of a material (e.g. vitreous carbon) that decomposes in the context of a heat treatment being applied onto layers 11e, 11f that delimit the cavities to be produced. The area coverage of the layers made of the material that decomposes is, for example, decreased from one printing step to another. The area coverage of the printed layers made of a material that decomposes upon heat treatment is selected, in principle, to be smaller than the area coverage of solid electrolyte layers 11d, 11g that are to be produced; the remaining surface is made, for example, of a suitable solid electrolyte material.

A further possibility is to apply different materials that decompose upon heat treatment, the materials that decompose each being printed on in a substantially parallelepiped structure. What is applied in the edge regions of cavities 25, 27 that are to be produced is a material that has a lower density per unit area than the material applied in the central regions of cavities 25, 27 that are to be produced. Upon subsequent heat treatment, the applied material decomposes and leaves behind cavities 25, 27; because of the lower density of the material applied in the edge regions of cavities 25, 27, the latter exhibit a height that diminishes continuously toward the lateral limits of the cavity.

Figure 3:
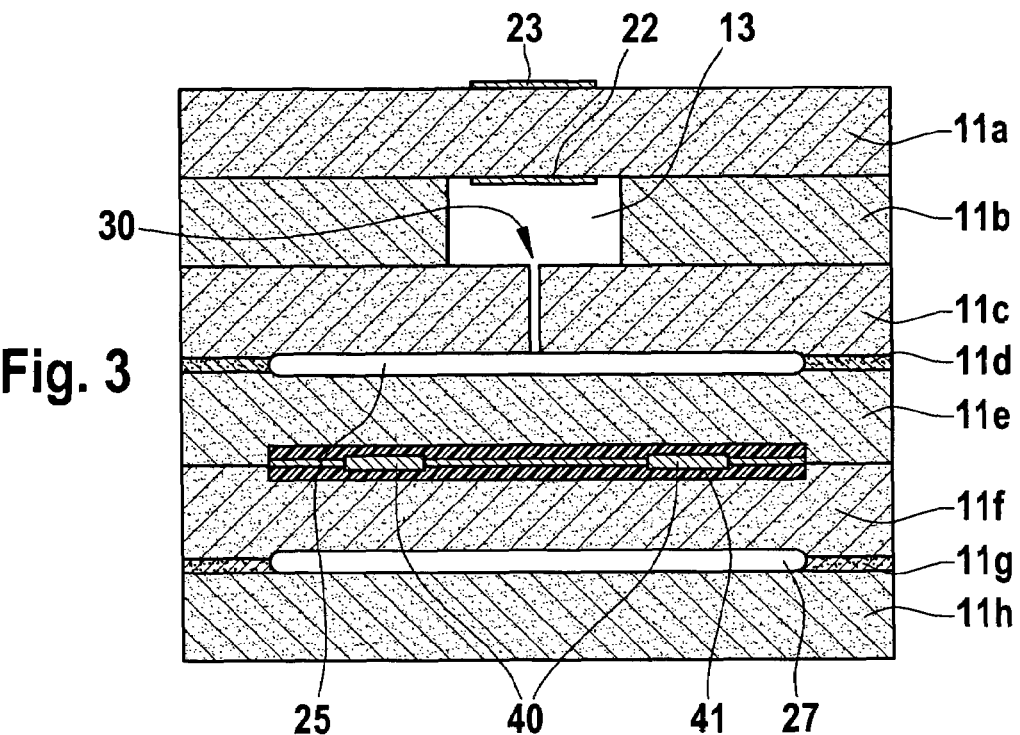
FIG. 3 shows a cross-sectional view of a second example embodiment of a sensor element according to the present invention.

A further decrease in the tensile stresses that occur during heating-up processes in solid electrolyte layer 11c that delimits cavity 25 on its side facing away from resistance heater 40 can be achieved if that layer locally has, e.g., in the longitudinal direction of the sensor element, a slit-shaped opening 30. An example embodiment of this kind is depicted in FIG. 3, in which identical reference characters once again refer to identical components as those shown in FIGS. 1 and 2. As a result of the formation of a slit-shaped opening 30, compressive stresses in solid electrolyte layer 11e located between resistance heater 40 and cavity 25 are diminished, and tensile stresses in solid electrolyte layer 11c delimiting cavity 25 on its side facing away from resistance heater 40 are thereby avoided.

This effect can also be achieved if, instead of an opening 30, simply a recess in the form of a groove, e.g., extending in the longitudinal direction of the sensor element, is embodied in solid electrolyte layer 11c. Opening 30, or a corresponding groove, is provided centrally in solid electrolyte layer 11c. Alternatively, it is possible to provide multiple openings or recesses within the same solid electrolyte layer. In addition, solid electrolyte layer 11h delimiting second cavity 27 on its side facing away from resistance heater 40 can also be equipped with a corresponding opening or recess. Opening 30 is produced in solid electrolyte layer 11c by stamping or milling a corresponding slit. If solid electrolyte layer 11c is a printed layer, a corresponding slit is already provided in the layout. Opening 30 functions in the sensor element as an expansion joint.

Figure 4:
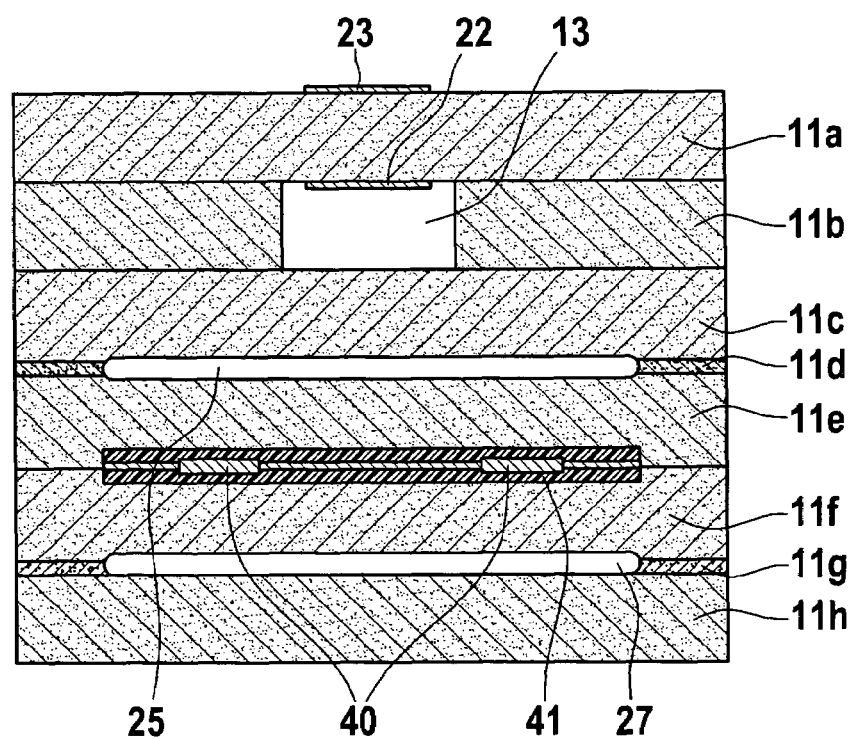
FIG. 4 shows a cross-sectional view of a third example embodiment of a sensor element according to the present invention.

A third example embodiment of the present invention is depicted in FIG. 4. Once again, identical reference characters designate identical components shown in FIGS. 1-3. In this sensor element, solid electrolyte layers 11c, 11h delimiting cavities 25, 27 on their sides facing away from resistance heater 40 are provided using a material that has a higher thermal conductivity than the solid electrolyte material of solid electrolyte layers 11e, 11f located between resistance heater 40 and cavities 25, 27. This can be achieved, for example, by the addition of approximately 10 wt % aluminum oxide to the solid electrolyte material of layers 11e, 11f. The result is that upon heating of the sensor element, lower compressive stresses occur in solid electrolyte layers 11e, 11f because of their lesser thermal expansion, and lower tensile stresses thus occur in solid electrolyte layers 11c, 11h.

Figure 5:
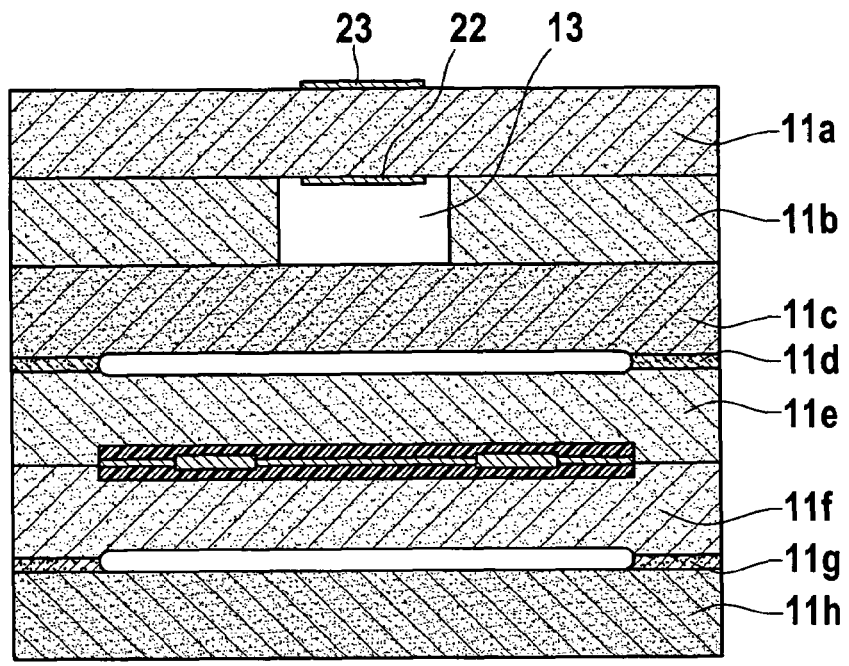
FIG. 5 shows a cross-sectional view of a fourth example embodiment of a sensor element according to the present invention.

A fourth example embodiment of the sensor element according to the present invention is depicted in FIG. 5. Once again, identical reference characters designate components identical to those in FIGS. 1 to 4. In this sensor element, solid electrolyte layers 11c, 11h delimiting cavities 25, 27 on their sides facing away from resistance heater 40 are provided using a material that has a lower modulus of elasticity than the solid electrolyte material of solid electrolyte layers 11e, 11f located between resistance heater 40 and cavities 25, 27. This can be achieved, for example, by way of a higher concentration of pore formers, for example 2 to 10 wt %, in solid electrolyte layers 11c, 11h during manufacture of the sensor element. In this embodiment as well, upon heating of the sensor element, lower compressive stresses occur in solid electrolyte layers 11e, 11f because of their lower modulus of elasticity, and lower tensile stresses thus occur in solid electrolyte layers 11c, 11h.

It is alternatively possible to embody solid electrolyte layers 11c, 11h from films having a higher tensile strength. This is achieved, for example, by reducing the concentration of stabilizing yttrium oxide as compared with the material of the other solid electrolyte layers, e.g., 3 mol % instead of 4.5 mol %.

Figure 6:
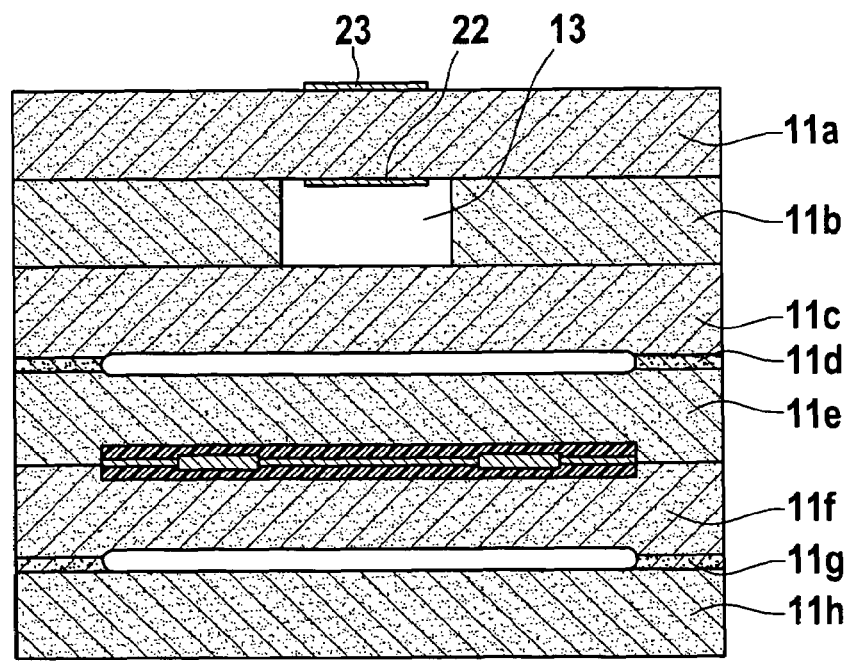
FIG. 6 shows a cross-sectional view of a fifth example embodiment of a sensor element according to the present invention.

FIG. 6 depicts a fifth example embodiment of a sensor element according to the present invention. Identical reference characters designate components identical to those in FIGS. 1 to 5. In this example, solid electrolyte layers 11d, 11g, which are produced from a film binder material during manufacture of the sensor element, are given an elevated tensile strength. This is achieved, for example, by reducing the concentration of stabilizing yttrium oxide as compared with the material of the other solid electrolyte layers, e.g., 3 mol % instead of 4.5 mol %. The result of this is that solid electrolyte layers 11c, 11e and 11f, 11h, adjacent to solid electrolyte layers 11d, 11g, can move to a greater extent relative to one another as the sensor element heats up. This once again decreases tensile and compressive stresses in these layers.

The sensor element according to the present invention and the method for its manufacture are not limited to the example embodiments set forth above, but rather further embodiments are conceivable, for example sensor elements that alternatively or additionally have electrochemical pump cells, or contain further solid electrolyte layers or cavities. Also conceivable is an application to sensor elements that serve to determine other gases, for example oxides of nitrogen, oxides of sulfur, ammonia, or hydrocarbons.

What is claimed is:

1. A sensor element for determining a concentration of a gas component in a gas mixture, comprising:
    at least one electrochemical measurement cell having a first electrode and a second electrode in contact with a solid electrolyte material;
    a heating element for heating the sensor element to operating temperature; and
    at least one cavity defined within the sensor element;
wherein:
    the at least one cavity has a diameter in at least one region close to a lateral delimiting surface of the cavity that is greater than zero and smaller than a diameter of a central region of the cavity; and at least one of longitudinal edges of the at least one cavity is rounded.

2. The sensor element as recited in claim 1, wherein the at least one cavity is hermetically sealed.

3. The sensor element as recited in claim 2, wherein the at least one cavity is located between the heating element and at least one of the first electrode and the second electrode.

4. A sensor element for determining a concentration of a gas component in a gas mixture, comprising:
at least one electrochemical measurement cell having a first electrode and a second electrode in contact with a solid electrolyte material;
a heating element for heating the sensor element to operating temperature; and
at least one cavity defined within the sensor element;
wherein:
the at least one cavity has a diameter in at least one region close to a lateral delimiting surface of the cavity that is greater than zero and smaller than a diameter of a central region of the cavity;
the at least one cavity is delimited by a ceramic layer of the sensor element; and
the ceramic layer has one of an opening and a recess aside from the at least one cavity.

5. A sensor element for determining a concentration of a gas component in a gas mixture, comprising:
at least one electrochemical measurement cell having a first electrode and a second electrode in contact with a solid electrolyte material;
a heating element for heating the sensor element to operating temperature; and
at least one cavity defined within the sensor element;
wherein:
the at least one cavity has a diameter in at least one region close to a lateral delimiting surface of the cavity that is greater than zero and smaller than a diameter of a central region of the cavity;
the at least one cavity is delimited by a ceramic layer of the sensor element;
the ceramic layer has one of an opening and a recess aside from the at least one cavity; and
the one of the opening and the recess is slit-shaped.

6. A sensor element for determining a concentration of a gas component in a gas mixture, comprising:
at least one electrochemical measurement cell having a first electrode and a second electrode in contact with a solid electrolyte material;
a heating element for heating the sensor element to operating temperature; and
a least one cavity defined within the sensor element;
wherein:
the at least one cavity:
has a diameter in at least one region close to a lateral delimiting surface of the cavity that is greater than zero and smaller than a diameter of a central region of the cavity; and
is delimited by a first ceramic layer on a side of the cavity facing away from the heating element and a second ceramic layer on a side of the cavity facing toward the heating element;
at least one of longitudinal edges of the at least one cavity is one of rounded and chamfered; and
a material of the first ceramic layer exhibits a greater thermal expansion than a material of the second ceramic layer.

7. A sensor element for determining a concentration of a gas component in a gas mixture, comprising:
at least one electrochemical measurement cell having a first electrode and a second electrode in contact with a solid electrolyte material;
a heating element for heating the sensor element to operating temperature; and
a least one cavity defined within the sensor element;
wherein:
the at least one cavity:
has a diameter in at least one region close to a lateral delimiting surface of the cavity that is greater than zero and smaller than a diameter of a central region of the cavity; and
is delimited by a first ceramic layer on a side of the cavity facing away from the heating element and a second ceramic layer on a side of the cavity facing toward the heating element;
at least one of longitudinal edges of the at least one cavity is one of rounded and chamfered; and
a material of the first ceramic layer has a higher modulus of elasticity than a material of the second ceramic layer.

8. A sensor element for determining a concentration of a gas component in a gas mixture, comprising:
at least one electrochemical measurement cell having a first electrode and a second electrode in contact with a solid electrolyte material; a heating element for heating the sensor element to operating temperature; and
a least one cavity defined within the sensor element;
wherein:
the at least one cavity:
has a diameter in at least one region close to a lateral delimiting surface of the cavity that is greater than zero and smaller than a diameter of a central region of the cavity; and
is delimited by a first ceramic layer on a side of the cavity facing away from the heating element and a second ceramic layer on a side of the cavity facing toward the heating element;
at least one of longitudinal edges of the at least one cavity is one of rounded and chamfered; and
a material of the first ceramic layer has a higher tensile strength than a material of the second ceramic layer.

9. The sensor element as recited in claim 8, wherein a third ceramic layer is located between the first ceramic layer and the second ceramic layer, and wherein a material of the third ceramic layer has a higher tensile strength than the material of the first ceramic layer and the material of the second ceramic layer.

10. The sensor element as recited in claim 6, wherein the at least one cavity is hermetically sealed.

11. The sensor element as recited in claim 10, wherein the at least one cavity is located between the heating element and at least one of the first electrode and the second electrode.

12. The sensor element as recited in claim 7, wherein the at least one cavity is hermetically sealed.

13. The sensor element as recited in claim 12, wherein the at least one cavity is located between the heating element and at least one of the first electrode and the second electrode.

14. The sensor element as recited in claim 13, wherein:
the ceramic layers are of the sensor element; and
at least one of the ceramic layers has one of an opening and a recess aside from the at least one cavity.

15. The sensor element as recited in claim 8, wherein the at least one cavity is hermetically sealed.

16. The sensor element as recited in claim 15, wherein the at least one cavity is located between the heating element and at least one of the first electrode and the second electrode.

17. The sensor element as recited in claim 16, wherein:
the ceramic layers are of the sensor elements; and
at least one of the ceramic layers has one of an opening and a recess aside from the at least one cavity.

18. The sensor element as recited in claim 5, wherein at least one of longitudinal edges of the at least one cavity is one of rounded and chamfered.

19. The sensor element as recited in claim 6, wherein the at least one of the longitudinal edges of the at least one cavity is rounded.

* * * * *